United States Patent [19]

Okamoto et al.

[11] 4,069,318

[45] * Jan. 17, 1978

[54] N²-ALKOXYNAPHTHALENESULFONYL-L-ARGININAMIDES AND THE PHARMACEUTICALLY ACCEPTABLE SALTS THEREOF

[75] Inventors: Shosuke Okamoto; Akiko Hijikata, both of Kobe; Ryoji Kikumoto, Machida; Yoshikuni Tamao, Yokohama; Kazuo Ohkubo, Machida; Tohru Tezuka, Yokohama; Shinji Tonomura, Tokyo, all of Japan

[73] Assignees: Mitsubishi Chemical Industries Ltd., Tokyo; Shosuke Okamoto, both of Japan

[*] Notice: The portion of the term of this patent subsequent to Apr. 19, 1994, has been disclaimed.

[21] Appl. No.: 760,727

[22] Filed: Jan. 19, 1977

Related U.S. Application Data

[63] Continuation-in-part of Ser. No. 646,522, Jan. 5, 1976, which is a continuation-in-part of Ser. No. 671,436, March 29, 1976, which is a continuation-in-part of Ser. No. 622,390, Oct. 14, 1975, abandoned.

[30] Foreign Application Priority Data

| Nov. 8, 1974 | Japan | 49-128774 |
| Nov. 8, 1974 | Japan | 49-128775 |
| Nov. 29, 1974 | Japan | 49-136695 |
| Nov. 29, 1974 | Japan | 49-136697 |
| Feb. 25, 1975 | Japan | 50-023268 |
| Feb. 26, 1975 | Japan | 50-023635 |

[51] Int. Cl.² ............ A61K 37/00; C07C 103/52
[52] U.S. Cl. .................... 424/177; 260/112.5 R
[58] Field of Search .............. 260/112.5 R; 424/177

[56] References Cited

U.S. PATENT DOCUMENTS

| 3,131,174 | 4/1964 | Schwyzer | 260/112.5 R |
| 4,018,913 | 4/1977 | Okamoto et al. | 260/112.5 R |
| 4,018,915 | 4/1977 | Okamoto et al. | 260/112.5 R |

Primary Examiner—Delbert R. Phillips
Attorney, Agent, or Firm—Oblon, Fisher, Spivak, McClelland & Maier

[57] ABSTRACT

N²-alkoxynaphthalenesulfonyl-L-argininamides and the pharmaceutically acceptable salts thereof have been found to be effective as pharmaceutical agents for the inhibition and suppression of thrombosis in mammals, and are prepared by reacting N²-alkoxynaphthalenesulfonyl-L-arginyl halide with a secondary amine.

4 Claims, No Drawings

N²-ALKOXYNAPHTHALENESULFONYL-L-ARGININAMIDES AND THE PHARMACEUTICALLY ACCEPTABLE SALTS THEREOF

CROSS REFERENCE TO RELATED APPLICATIONS

This application is a CIP Application of U.S. Pat. Application, Ser. No. 646,522, filed on Jan. 5, 1976, now allowed, which is a CIP Application of U.S. Patent Application Ser. No. 671,436, filed on Mar. 29, 1976, which is a CIP Application of U.S. Pat. Application Ser. No. 622,390, filed on Oct. 14, 1975, now abandoned.

BACKGROUND OF THE INVENTION

1. Field of the Invention

This invention relates to the discovery of certain new and useful N²-alkoxynaphthalenesulfonyl-L-argininamides and the pharmaceutically acceptable salts thereof, which are of especial value in view of their outstanding antithrombotic properties and low toxicities.

2. Description of the Prior Art

In the past, there have been many attempts to obtain new and improved agents for the treatment of thrombosis. The N²-(p-tolylsulfonyl)-L-arginine esters have been found to be one type of agent which can be used and these have been found to be effective in dissolving blood clots. (U.S. Pat. No. 3,622,615, issued Nov. 23, 1971.) One family of compounds, which have been found to be particularly useful as highly specific inhibitors of thrombin for the control of thrombosis is the N²-dansyl-L-arginine ester or amide. (Our pending U.S. application Ser. No. 496,939, filed Aug. 13, 1974, now U.S. Pat. No. 3,978,045.) However, there is a continuing need for a highly specific inhibitor of thrombin for the control of thrombosis, which exhibits lower toxicity.

SUMMARY OF THE INVENTION

It has now been discovered that N²-alkoxynaphthalenesulfonyl-L-argininamides exhibit antithrombotic activity and even lower toxicity levels at the same relative potencies, as compared with the N²-dansyl-L-arginine ester or amide.

The compounds of this invention can be represented by the formula (I):

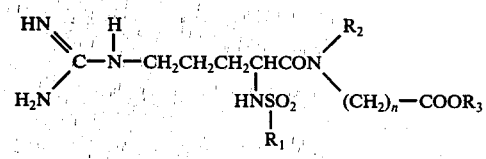

wherein $R_1$ is naphthyl substituted with at least one $C_1-C_5$ alkoxy; $R_2$ is $C_7-C_{15}$ aralkyl; $R_3$ is selected from the group consisting of hydrogen, $C_1-C_{10}$ alkyl, $C_6-C_{10}$ aryl and $C_7-C_{12}$ aralkyl; and $n$ is an integer of 1, 2, or 3. Also encompassed within this invention are pharmaceutically acceptable salts thereof. This invention also relates to a method for inhibiting activity and suppressing activation of thrombin in vivo in mammals, which comprises administering to a mammal a pharmaceutically (antithiambatically) effective amount of an N²-alkoxynaphthalenesulfonyl-L-argininamide or the pharmaceutically acceptable salt thereof. Another aspect of this invention relates to a process for producing N²-alkoxynaphthalenesulfonyl-L-argininamides, which comprises reacting an N²-alkoxynaphthalenesulfonyl-L-arginyl halide with a corresponding secondary amine.

DETAILED DESCRIPTION OF THE PREFERRED EMBODIMENTS

This invention relates to a group of N²-alkoxynaphthalenesulfonyl-L-argininamides of the formula (I):

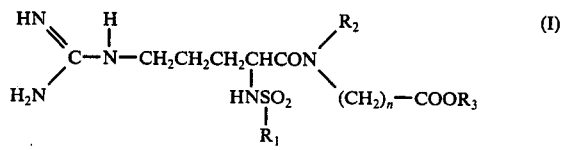

wherein $R_1$ is an alkoxynaphthyl wherein the alkoxy groups have 1–5 (preferably 1–3) carbon atoms, such as methoxy, ethoxy, propoxy, isopropoxy, butoxy, sec-butoxy, tert-butoxy, pentyloxy and the like. Preferred are those naphthyl groups having one or two alkoxy substituents, when two or more alkoxy groups are present, each may be the same or different; $R_2$ is aralkyl of 7–15 (preferably 7–10) carbon atoms, such as benzyl, phenethyl, 3-phenylpropyl, 4-phenylbutyl, 6-phenylhexyl, 1-phenylethyl, 2-phenylpropyl and the like; $R_3$ is selected from the group consisting of hydrogen, alkyl of 1–10 (preferably 1–6) carbon atoms, such as methyl, ethyl, propyl, butyl, tert-butyl, hexyl, octyl, decyl and the like, $C_6-C_{10}$ aryl such as phenyl and naphthyl, m-tolyl, p-tolyl, ethylphenyl and butylphenyl, preferably phenyl and m-tolyl, and aralkyl of 7–12 (preferably 7–10) carbon atoms, such as benzyl, phenethyl and the like; and $n$ is an integer of 1, 2 or 3.

Suitable illustrations of $R_1$ in the above formula (I) are 5-methoxyl-1-naphthyl, 6-methoxy-2-naphthyl, 7-methoxy-2-naphthyl, 4,6-dimethoxy-2-naphthyl, 6,7-dimethoxy-2-naphthyl and 6,7-diethoxy-2-naphthyl. Suitable $R_2$ groups in the above formula (I) are benzyl, phenethyl and 3-phenylpropyl. Suitable —(CH₂)ₙ—COOR₃ groups in the above formula (I) are carboxymethyl, 2-carboxyethyl, 3-carboxypropyl, ethoxycarbonylmethyl, tert-butoxycarbonylmethyl, phenoxycarbonylmethyl, benzyloxycarbonylmethyl, 2-ethoxycarbonylethyl, 2-tert-butoxycarbonylethyl, and 3-tert-butoxycarbonylpropyl. Illustrative of suitable N²-alkoxynaphthalenesulfonyl-L-argininamides of sufficient activity of this invention are the following:

N²-(6,7-dimethoxy-2-naphthalenesulfonyl)-L-arginyl-N-benzylglycine

N²-(6,7-dimethoxy-2-naphthalenesulfonyl)-L-arginyl-N-benzylglycine tert-butyl ester N²-(6,7-dimethoxy-2-naphthalenesulfonyl)-L-arginyl-N-phenethylglycine N²-(6,7-dimethoxy-2-naphthalenesulfonyl)-L-arginyl-N-phenethylglycine tert-butyl ester N²-(6,7-dimethoxy-2-naphthalenesulfonyl)-L-arginyl-N-benzyl-β-alanine N²-(6,7-dimethoxy-2-naphthalenesulfonyl)-L-arginyl-N-benzyl-β-alanine tert-butyl ester N²-(6,7-dimethoxy-2-naphthalenesulfonyl)-L-arginyl-N-phenethyl-β-alanine N²-(6,7-dimethoxy-2-naphthalenesulfonyl)-L-arginyl-N-phenethyl-β-alanine tert-butyl ester N²-(4,6-dimethoxy-2-naphthalenesulfonyl)-L-arginyl-N-benzylglycine N²-(4,6-dimethoxy-2-naphthalenesulfonyl)-L-arginyl-N-benzylglycine tert-butyl ester N²-(7-methoxy-2-naphthalenesulfonyl)-L-arginyl-N-phenethyl-glycine N²-(7-methoxy-2-naphthalenesulfonyl)-L-arginyl-N-phenethyl-glycine tert-butyl ester N²-(7-methoxy-2-naphthalenesulfonyl)-L-arginyl-N-benzyl-β-alanine N²-(7-methoxy-2-naphthalenesulfonyl)-L-arginyl-N-benzyl-β-alanine tert-butyl ester N²-(6-methoxy-2-naphthalenesulfonyl)-N-benzyl-N-(3-carboxypropyl)-L-argininamide N²-(6-methoxy-2-naphthalenesulfonyl)-N-benzyl-N-(3-tert-butoxycarbonylpropyl)-L-argininamide N²-(5-methoxy-1-naphthalenesulfonyl)-L-arginyl-N-benzylglycine N²-(5-methoxy-1-naphthalenesulfonyl)-L-arginyl-N-benzylglycine tert-butyl ester The pharmaceutically acceptable salts of the above compounds are of course, also included within the scope of this invention. The above compounds are intended only to illustrate the variety of structures which can be used in the process of this invention, and the above listing is not to be construed as limiting the scope of the invention. These typical compounds are highly potent in their antithrombotic activity.

For the preparation of the compounds of this invention, various methods can be employed depending upon the particular starting materials and/or intermediates involved. Successful preparation of these compounds is possible by way of several synthetic routes which are outlined below.

a. Condensation of an L-argininamide with an alkoxynaphthalenesulfonyl halide

This process may be illustrated as follows:

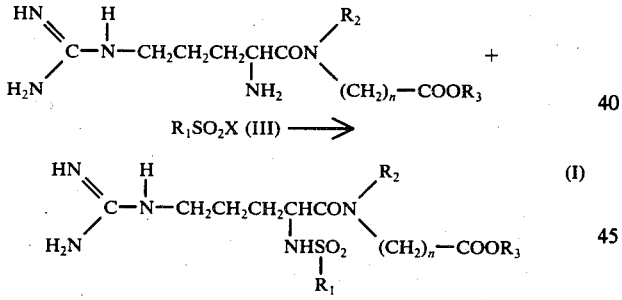

In the above formulas, $R_1$, $R_2$, and $R_3$ and $n$ are as defined herein above, and X is halogen.

The N²-alkoxynaphthalenesulfonyl-L-argininamide (I) is prepared by the condensation of an L-argininamide (II) with a substantially equimolar amount of an alkoxynaphthalenesulfonyl halide (III), preferably chloride. The condensation reaction is generally effected in a suitable reaction-inert solvent in the presence of an excess of a base, such as an organic base (triethylamine, pyridine) or a solution of an inorganic base (sodium hydroxide, potassium carbonate), at a temperature of 0° C to the boiling temperature of the solvent for a period of 10 minutes to 15 hours. The preferred solvents for the condensation include benzenediethyl ether, diethyl ether-water and dioxane-water. After the reaction is complete, the salt formed is extracted with water, and the solvent is removed by such standard means as evaporation under reduced pressure to give the N²-alkoxynaphthalenesulfonyl-L-argininamide (I), which can be purified by trituration or recrystallization from a suitable solvent, such as diethyl ethertetrahydrofuran, diethyl ether-methanol and water-methanol, or may be chromatographed on silica gel.

The L-argininamides (II) starting materials required for the condensation reaction can be prepared by protecting the guanidino and α-amino groups of the L-arginine via nitration, acetylation, formylation, phthaloylation, trifluoroacetylation, p-methoxybenzyloxycarbonylation, benzoylation, benzyloxycarbonylation, tert-butoxycarbonylation or tritylation and then condensing the formed N^G-substituted-N²-substituted-L-arginine with a corresponding secondary amine by such a conventional process as the acid chloride method, azide method, mixed anhydride method, activated ester method or carbodiimide method, and thereafter selectively removing the protective groups.

b. Removal of the N^G-substituent from an N^G-substituted-N²-alkoxynaphthalenesulfonyl-L-argininamide This process may be illustrated as follows:

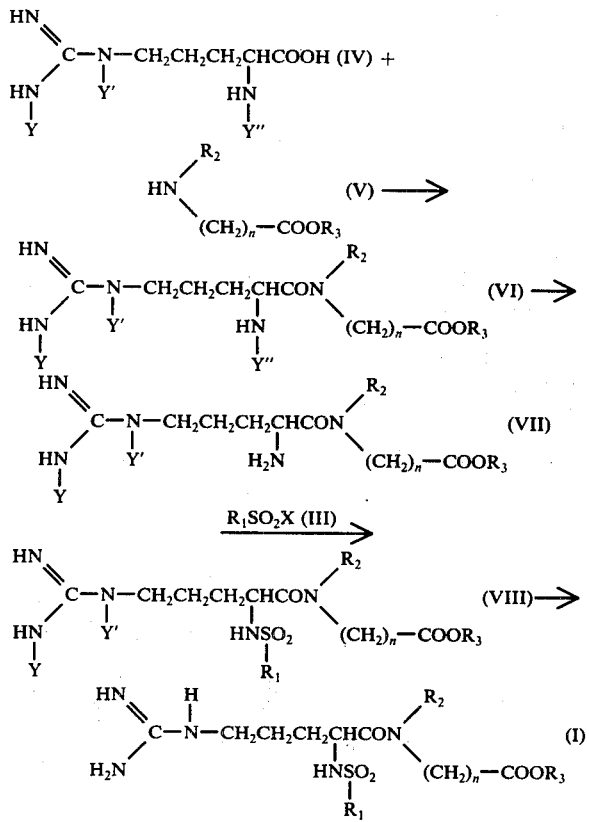

In the above formulas, $R_1$, $R_2$, $R_3$, X and $n$ are as defined herein above; Y" is a protective group for the amino group, such as benzyloxycarbonyl or tert-butoxycarbonyl; and Y and Y' are hydrogen and protective groups for the guanidino group, such as nitro, tosyl, trityl, oxycarbonyl or the like. At least one of Y and Y' is a protective group for the guanidino group.

The N²-alkoxynaphthalenesulfonyl-L-argininamide (I) is prepared by removing the N^G-substitutent from an N^G substituted-N²-alkoxynaphthalenesulfonyl-L-argininamide (VIII) by means of acidolysis or hydrogenolysis. The acidolysis is generally effected by contacting the N^G-substituted-N²-alkoxynaphthalenesulfonyl-L-argininamide (VIII) and an excess of an acid such as hydrogen fluoride, hydrogen chloride, hydrogen bromide or trifluoroacetic acid, without a solvent or in a solvent, such as an ether (tetrahydrofuran, dioxane), an alcohol (methanol, ethanol) or acetic acid at a temperature of −10° C to 100° C, and preferably at room temperature for a period of 30 minutes to 24 hours. The products are isolated by evaporation of the solvent and the excess acid, or by trituration with a suitable solvent followed by filtration and drying. Because of the use of the excess acid, the products are generally the acid addition salts of the $N^2$-alkoxynaphthalenesulfonyl-L-argininamides (I), which can be easily converted to a free amide by neutralization. The removal of the nitro group and the oxycarbonyl group, e.g., benzyloxycarbonyl, p-nitrobenzyloxycarbonyl, is readily accomplished by hydrogenolysis. The hydrogenolysis is effected in a reaction-inert solvent, e.g., methanol, ethanol, tetrahydrofuran or dioxane, in the presence of a hydrogen-activating catalyst, e.g., Raney nickel, palladium, or platinum, in a hydrogen atmosphere at a temperature of 0° C to the boiling temperature of the solvent for a period of 2 hours to 120 hours. The hydrogen pressure is not critical, and atmospheric pressure is sufficient. The $N^2$-alkoxynaphthalenesulfonyl-L-argininamides (I) are isolated by filtration of the catalyst followed by evaporation of the solvent. The $N^2$-alkoxynaphthalenesulfonyl-L-argininamides can be purified in the same manner as described above.

The $N^G$-substituted-$N^2$-alkoxynaphthalenesulfonyl-L-argininamides (VIII) starting materials can be prepared by condensing an $N^G$-substituted-$N^2$-substituted L-arginine (IV) (generally the $N^2$-substituent is a protective group for the amino group, such as benzyloxycarbonyl, tert-butoxycarbonyl, or the like) and a corresponding secondary amine (V) via the azide method, mixed anhydride method, activated ester method, carbodiimido method or the like, selectively removing only the $N^2$-substituent of an $N^G$-substituted-$N^2$-substituted L-argininamide (VI) by means of catalytic hydrogenolysis or acidolysis, and then condensing the thus obtained $N^G$-substituted-L-argininamide (VII) with an alkoxynaphthalenesulfonyl halide (III), preferably a chloride in the presence of a base in a solvent. These reaction conditions are as described above in the condensation of an L-argininamide with an alkoxynaphthalenesulfonyl halide, and the removal of the $N^G$-substituent from an $N^G$-substituted-$N^2$-alkoxynaphthalenesulfonyl-L-argininamide.

c. Condensation of an $N^2$-alkoxynaphthalenesulfonyl-L-arginyl halide with an amine This process may be illustrated as follows:

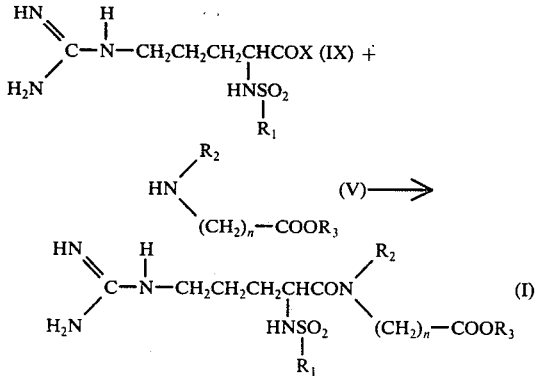

In the above formulas, $R_1$, $R_2$, $R_3$, X and $n$ are as defined herein above.

The $N^2$-alkoxynaphthalenesulfonyl-L-arginamide (I) is prepared by the condensation of an $N^2$-alkoxynaphthalenesulfonyl-L-arginyl halide (IX), preferably a chloride, with at least an equimolar amount of a secondary amine (V). The condensation reaction can be carried out without an added solvent. However, satisfactory results will be obtained with the use of a solvent such as basic solvents (dimethylformamide, dimethylacetamide, etc.) or halogenated solvents (chloroform, dichloromethane, etc.). The amount of the solvents to be used is not critical and may vary from about 5 to 100 times the weight of the $N^2$-alkoxynaphthalenesulfonyl-L-arginyl halide (IX). Preferred condensation reaction temperatures are in the range of from −10° C to room temperature. The reaction time is not critical, but varies with the secondary amine (V) employed. In general, a period of from 5 minutes to 10 hours is operable. The $N^2$-alkoxynaphthalenesulfonyl-L-argininamide obtained can be isolated and purified in the same manner as described above.

The $N^2$-alkoxynaphthalenesulfonyl-L-arginyl halide (IX) starting materials required for the condensation reaction can be prepared by reacting an $N^2$-alkoxynaphthalenesulfonyl-L-arginine with at least an equimolar amount of a halogenating agent such as thionyl chloride, phosphorous oxychloride, phosphorus trichloride, phosphorous pentachloride or phosphorus tribromide. The halogenation can be carried out with or without an added solvent. The preferred solvents are chlorinated hydrocarbons such as chloroform and dichloromethane, and ethers such as tetrahydrofuran and dioxane. The amount of the solvent to be used is not critical and may vary from about 5 to 100 times the weight of the $N^2$-alkoxynaphthalenesulfonyl-L-arginine. Preferred reaction temperatures are in the range of −10° C to room temperature. The reaction time is not critical, but varies with the halogenating agent and reaction temperature. In general, a period of 15 minutes to 5 hours is operable.

The $N^2$-alkoxynaphthalenesulfonyl-L-arginines which are the starting materials for the preparation of $N^2$-alkoxynaphthalenesulfonyl-L-arginyl halides (IX) may include some new compounds, which can be conventionally prepared by the condensation of L-artinine with a substantially equimolar amount of the alkoxynaphthalenesulfonyl halide (III) by a method similar to that described in the condensation of an L-argininamide with a naphthalenesulfonyl halide.

d. Guanidylation of an $N^2$-alkoxynaphthalenesulfonyl-L-ornithinamide or an acid addition salt thereof This process may be illustrated as follows:

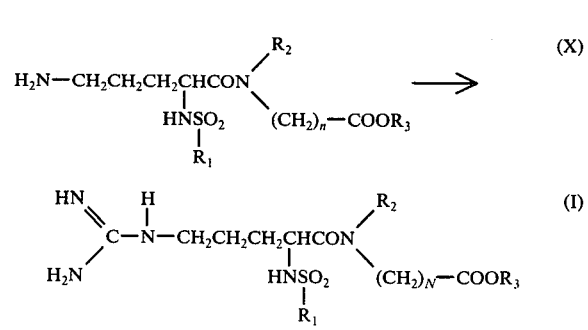

In the above formulas, $R_1$, $R_2$, $R_3$ and $n$ are as defined herein above.

The $N^2$-alkoxynaphthalenesulfonyl-L-argininamide (I) is prepared by guanidylating an $N^2$-alkoxynaphthalenesulfonyl-L-ornithinamide (X) with an ordinary guanidylating agent such as an O-alkylisourea, S-alkylisothiourea, 1-guanyl-3,5-dimethylpyrazole or carbodiimide. The preferred guanidylating agents are the O-alkylisourea and the S-alkylisothiourea. The guanidylation of the $N^2$-alkoxynaphthalenesulfonyl-L-ornithinamide (X) with the O-alkylisourea or S-alkylisothiourea is generally effected in a solvent in the presence of a base at a temperature of from 0° C to the boiling temperature of the solvent for a period of from 30 minutes to 50 hours. Examples of preferred bases include triethylamine, pyridine, sodium hydroxide and sodium methoxide. The base is used in an amount of from 0.01 to 0.1 equivalent based on the amount of the $N^2$-alkoxynaphthalenesulfonyl-L-ornithinamide. Examples of preferred solvents include water, water-ethanol and water-dioxane. After the reaction is complete, the $N^2$-alkoxynaphthalenesulfonyl-L-argininamide (I) is isolated by evaporation of the solvent followed by removal of the excess base and the salt formed by a water wash.

It is well recognized in the art that an ester derivative of the $N^2$-alkoxynaphthalenesulfonyl-L-argininamide (I) wherein $R_3$ is alkyl, aryl or aralkyl, can be prepared from a carboxylic acid derivative of the $N^2$-alkoxynaphthalenesulfonyl-L-argininamide wherein $R_3$ is hydrogen, by the conventional esterification methods well known to those skilled in the art. It is also well recognized in the art that the carboxylic acid derivative can be prepared from the ester derivative by the conventional hydrolysis or acidolysis methods. The conditions under which esterification, hydrolysis or acidolysis would be carried out will be each apparent to those skilled in the art.

The $N^2$-alkoxynaphthalenesulfonyl-L-argininamides (I) of this invention form acid addition salts with any of a variety of inorganic and organic acids. Some of the $N^2$-alkoxynaphthalenesulfonyl-L-argininamides containing a free carboxy group, wherein $R_3$ is hydrogen, form salts with any of a variety of inorganic and organic bases. The product of the reactions described above can be isolated in the free form or in the form of salts. In addition, the product can be obtained as pharmaceutically acceptable acid addition salts by reacting one of the free bases with an acid, such as hydrochloric, hydrobromic, hydroiodic, nitric, sulfuric, phophoric, acetic, citric, maleic, succinic, lactic, tartaric, gluconic, benzoic, methanesulfonic, ethanesulfonic, benzenesulfonic, p-toluenesulfonic acids or the like. In a similar manner, the product can be obtained as pharmaceutically acceptable salts by reacting one of the free carboxylic acids with a base, such as sodium hydroxide, potassium hydroxide, ammonium hydroxide, triethylamine, procaine, dibenzylamine, 1-ephenamine, N,N'-dibenzylethylenediamine, N-ethylpiperidine or the like. Likewise, treatment of the salts with a base or acid results in a regeneration of the free amide.

As stated above, the $N^2$-alkoxynaphthalenesulfonyl-L-argininamides, and the salts thereof of this invention are characterized by highly specific inhibitory activity in mammals against thrombin as well as a substantial lack of toxicity, and therefore these compounds are useful as diagnostic reagents in the determination of thrombin in blood, and/or for the medical control or prevention of thrombosis.

The antithrombotic activities of the $N^2$-alkoxynaphthalenesulfonyl-L-argininamide of this invention were compared with that of a known antithrombotic agent, $N^2$-(p-tolylsulfonyl)-L-arginine methyl ester, by determining the fibrinogen coagulation time. The measurement of the fibrinogen coagulation time was conducted as follows: An 0.8 ml aliquot of a fibrinogen solution, which had been prepared by dissolving 150 mg of bovine fibrinogen (Cohn fraction I) supplied by Armour Inc. in 40 ml of a borate saline buffer (pH 7.4), was mixed with 0.1 ml of a borate saline buffer, pH 7.4, (control) or a sample solution in the same buffer, and 0.1 ml of a thrombin solution (5 units/ml) supplied by Mochida Pharmaceutical Co., Ltd. was added to the solutions in an ice bath. Immediately after mixing, the reaction mixture was transferred from the ice bath to a bath maintained at 25° C. Coagulation times were taken as the period between the time of transference to the 25° C bath and the time of the first appearance of fibrin threads. In the cases where no drug samples were added, the coagulation time was 50–55 seconds. The experimental results are summarized in Table 1. The term "concentration required to prolong the coagulation time by a factor of two" is the concentration of an active ingredient required to prolong the normal coagulation time from 50–55 seconds to 100–110 seconds. The concentration required to prolong the coagulation time by a factor of two for the known antithrombotic agent, $N^2$-(p-tolylsulfonyl)-L-arginine methyl ester, was 1,100 $\mu$m. The inhibitors are shown in Table 1 by indication of $R_1$, $R_2$, $R_3$ and $n$ in the formula (I) and the addition moiety.

When a solution containing an $N^2$-alkoxynaphthalenesulfonyl-L-argininamide of this invention was administered intravenously into animal bodies, the high antithrombotic activity in the circulating blood was maintained for from one to three hours. The halflife for decay of the antithrombotic compounds of this invention in circulating blood was shown to be approximately 60 minutes; the physiological conditions of the host animals (rats, rabbits, dogs and chimpanzees) were well maintained. The experimental decrease of fibrinogen in the animals caused by infusion of thrombin was satisfactorily controlled by simultaneous infusion of the compounds of this invention.

The acute toxicity values ($LD_{50}$) determined by intraperitoneal administration of substances of formula (I) in mice (male, 20 g) range from about 1,000 to 10,000 milligrams per kilogram of body weight. Representative $LD_{50}$ values, for example, for $N^2$-(6,7-dimethoxy-2-naphthalenesulfonyl)-L-arginyl-N-benzylglycine, $N^2$-(6,7-dimethoxy-2-naphthalenesulfonyl)-L-arginyl-N-phenethylglycine, $N^2$-(4,6-dimethoxy-2-naphthalenesulfonyl)-L-arginyl-N-benzylglycine and $N^2$-(5-methoxy-1-naphthalenesulfonyl)-L-arginyl-N-benzylglycine are $>1,000$, $>1,500$, $>1,000$, $>1,000$ milligrams per kilogram, respectively. On the other hand, $LD_{50}$ values for $N^2$-dansyl-N-butyl-L-argininamide and $N^2$-dansyl-N-methyl-N-butyl-L-argininamide are 75 and 70 milligrams per kilogram, respectively.

The therapeutic agents of this invention may be administered to mammals, including humans, alone or in combination with pharmaceutically acceptable carriers, the proportion of which is determined by the solubility and chemical nature of the compound, the chosen route of administration and standard pharmaceutical practice.

For example, the compounds may be injected parenterally, that is, intramuscularly, intravenously or subcutaneously. For parenteral administration, the compounds may be used in the form of sterile solutions containing other solutes, for example sufficient saline or glucose to make the solution isotonic. The compounds may be administered orally in the form of tablets, capsules, or granules containing suitable excipients such as starch, lactose, white sugar and the like. The compounds may be administered sublingually in the form of troches or lozenges in which each active ingredient is mixed with sugar or corn syrups, flavoring agents and dyes, and then dehydrated sufficiently to make the mixture suitable for pressing into solid form. The compounds may be administered orally in the form of solutions which may contain coloring and flavoring agents.

Physicians will determine the dosage of the present therapeutic agents which will be most suitable for humans, and dosages vary with the mode of administration and the particular compound chosen. In addition, the dosage will vary with the particular patient under treatment. When the composition is administered orally, a larger quantity of the active agent will be required to produce the same effect as caused with a smaller quantity given parenterally. The therapeutic dosage is generally 10–50 mg/kg of active ingredient parenterally, 10–500 mg/kg orally per day.

Having generally described the invention, a more complete understanding can be obtained by reference to certain specific examples, which are included for purposes of illustration only and are not intended to be limiting unless otherwise specified.

EXAMPLE 1

$N^2$-(6,7-dimethoxy-2-naphthalenesulfonyl)-L-arginyl-N-phenethylglycine:

To a solution of 3.00 g of $N^G$-nitro-$N^2$-(6,7-dimethoxy-2-naphthalenesulfonyl)-L-arginyl-N-phenethylglycine benzyl ester in 50 ml of ethanol and 0.5 ml of acetic acid was added 0.5 g of palladium-black and then the mixture was shaken in a hydrogen atmosphere for 100 hours at room temperature. At the end of this period, the ethanol solution was filtered to remove the catalyst and evaporated to dryness. The residue was washed several times with dry diethyl ether and chromatographed on 80 ml of Daiaion ® SK 102 ion exchange resin (200–300 mesh, H+ form, manufactured by Mitsubishi Chemical Industries Limited) packed in water, washed with water, and eluted with 3% ammonium hydroxide solution. The fraction eluted from 3% ammonium hydroxide was evaporated to dryness to give 1.71 g (70%) of $N^2$-(6,7-dimethoxy-2-naphthalenesulfonyl)-L-arginyl-N-phenethylglycine as an amorphous solid.

I.R. (KBr): 3,360, 3,200, 1,590 cm$^{-1}$; Analysis — Calcd. for $C_{28}H_{35}N_5O_7S$ (percent): C, 57.42; H, 6.02; N, 11.96; Found (percent): C, 57.09; H, 6.06; N, 11.74.

EXAMPLE 2

$N^2$-(6,7-dimethoxy-2-naphthalenesulfonyl)-L-arginyl-N-benzylglycine

A. Sodium 6,7-dimethoxy-2-naphthalenesulfonate:

To a well stirred solution of 70.8 g of sodium 6,7-dimethoxy-2-naphthalenesulfonate and 77.2 g of sodium hydroxide in 450 ml of water was added dropwise 230 ml of dimethyl sulfate at 60° C over a period of one hour, during which time the product precipitated. To this reaction mixture was added in portions 38.8 g of sodium hydroxide, and stirring was continued for one hour. After one hour at room temperature, the precipitate was filtered, washed with ethanol and dried to give 50 g of sodium 6,7-dimethoxy-2-naphthalenesulfonate.

B. 6,7-dimethoxy-2-naphthalenesulfonyl chloride:

To a stirred suspension of 50 g of finely divided sodium 6,7-dimethoxy-2-naphthalenesulfonate in 100 ml of dimethylformamide was added dropwise 62.2 ml of thionyl chloride at room temperature. After 30 minutes, the reaction mixture was poured into 1 liter of ice water, and the precipitate filtered and then dissolved into 250 ml of benzene. The benzene solution was repeatedly washed with water and dried over anhydrous sodium sulfate. The solvent was evaporated to dryness in vacuo, and the residue was recrystallized from benzene-n-hexane (1 : 1) to give 32 g of 6,7-dimethoxy-2-naphthalenesulfonyl chloride, M.P. 127.5°–129.5° C.

Analysis — Calcd. for $C_{12}H_{11}O_4SCl$ (percent): C, 50.26; H, 3.87; Cl, 12.37; Found (percent): C, 50.45; H, 4.00; Cl, 12.33.

Certain of the dialkoxy naphthalene sulfonyl chlorides useful as starting materials herein also have not previously been reported in the chemical literature such as 6,7-dimethoxy-2-naphthalene-sulfonyl choride. However, this compound is also preparable by known procedures, such as are described by E. H. Rodd, *Chemistry of Carbon Compounds*, Elsevier Publishing Company, 1954, Volume III, pp. 441–469.

C. N-benzylglycine tert-butyl ester:

To 71.0 g of benzylamine in 100 ml of benzene was added with stirring 25.0 g of tert-butyl chloroacetate over a period of 30 minutes, while maintaining the temperature at 30°–70° C. The reaction mixture was held at 70° C for an additional one hour. At the end of this period, the reaction mixture was taken up in 70 ml of 2N NaOH solution and 80 ml of benzene, transferred into a separatory funnel and well shaken. The benzene solution was separated, washed with water, dried over anhydrous sodium sulfate and filtered. After evaporation of benzene, the residue was distilled under reduced pressure to give 32.7 g (89.0 percent) of N-benzylglycine tert-butyl ester, B.P. 120°–125° C/2 mmHg.

Analysis — Calcd. for $C_{13}H_{19}NO_2$ (percent): C, 70.56; H, 8.65; N, 6.33; Found (percent): C, 70.48; H, 8.67; N, 6.31.

D. $N^2$-(6,7-dimethoxy-2-naphthalenesulfonyl)-L-arginine:

To a well stirred solution of 83.6 g of L-arginine in 800 ml of 10% potassium carbonate solution was added 114.7 g of 6,7-dimethoxy-2-naphthalenesulfonyl chloride in 800 ml of benzene. The reaction mixture was stirred at 60° C for 5 hours, during which time the product precipitated. After one hour at room temperature, the precipitate was filtered and washed successively with benzene and water to give 129 g (76 percent) of $N^2$-(6,7-dimethoxy-2-naphthalenesulfonyl)-L-arginine, M.P. 252°–5° C.

E. $N^2$-(6,7-dimethoxy-2-naphthalenesulfonyl)-L-arginyl chloride:

A suspension of 2.0 g of $N^2$-(6,7-dimethoxy-2-naphthalenesulfonyl)-L-arginine in 20 ml of thionyl chloride was stirred for 2 hours at room temperature. Addition of cold dry diethyl ether resulted in a precipitate which was collected by filtration and washed several times with dry diethyl ether to give $N^2$-(6,7-dimethoxy-2-naphthalenesulfonyl)-L-arginyl chloride.

F. $N^2$-(6,7-dimethoxy-2-naphthalenesulfonyl)-L-arginyl-N-benzylglycine tert-butyl ester hydrosulfite:

To a stirred solution of 4.15 g of N-benzylglycine tert-butyl ester in 20 ml of chloroform was carefully added N²-(6,7-dimethoxy-2-naphthalenesulfonyl)-L-arginyl chloride obtained above. The reaction mixture was allowed to stand at room temperature for one hour. At the end of this period, the reaction mixture was washed twice with 20 ml of saturated sodium chloride solution and evaporated to dryness. The residue was triturated with a small amount of water to give a crystalline material. This was collected by filtration, washed with diethyl ether and recrystallized from ethanol-diethyl ether to give 2.67 g (85 percent) of N²-(6,7-dimethoxy-2-naphthalenesulfonyl)-L-arginyl-N-benzylglycine tert-butyl ester hydrosulfite, M.P. 189°–191° C, I.R. (KBr): 3,360, 3,160, 1,730 cm$^{-1}$.

Analysis — Calcd. for $C_{31}H_{41}O_7N_5S \cdot \frac{1}{2}H_2SO_3$ (percent): C, 55.68; H, 6.33; N, 10.47; Found (percent): C, 55.36; H, 6.35; N, 10.45.

The flavianate; M.P. 178°–180° C (dec.)
I.R. (KBr): 3,360, 3,200, 1,735 cm$^{-1}$; Analysis — Calcd. for $C_{31}H_{41}O_7S \cdot C_{10}H_6O_8N_2S$ (percent): C, 52.28; H, 5.03; N, 10.41; Found (percent): C, 52.26; H, 5.00; N, 10.36.

G. N²-(6,7-dimethoxy-2-naphthalenesulfonyl)-L-arginyl-N-benzylglycine:

To a solution of 2.00 g of N²-(6,7-dimethoxy-2-naphthalenesulfonyl)-L-arginyl-N-benzylglycine tert-butyl ester hydrosulfite in 20 ml of chloroform was added 50 ml of 15% HCl-ethyl acetate. The reaction mixture was stirred for 5 hours at room temperature. At the end of this period, the reaction mixture was evaporated to dryness. The residue was washed several times with dry diethyl ether and chromatographed on 80 ml of Daiaion ® SK 102 ion exchange resin (200–300 mesh, H+ form, manufactured by Mitsubishi Chemical Industries Limited) packed in water, washed with water and eluted with 3% ammonium hydroxide solution. The fraction eluted from 3% ammonium hydroxide solution was evaporated to dryness to give 1.20 g (70 percent) of N²-(6,7-dimethoxy-2-naphthalenesulfonyl)-L-arginyl-N-benzylglycine as an amorphous solid, I.R. (KBr): 3,370, 3,200, 1.615 cm$^{-1}$.

Analysis — Calcd. for $C_{27}H_{33}N_5O_7S$ (percent): C, 56.73; H, 5.82; N, 12.25; Found (percent): C, 56.43; H, 5.80; N, 12.19. Various other N²-alkoxynaphthalenesulfonyl-L-arginamides or acid addition salts thereof were synthesized in accordance with the procedure of the above examples, and the test results are summarized in Table 1. The following compounds are prepared in a similar manner:

N²-(6,7-dimethoxy-2-naphthalenesulfonyl)-L-arginyl-N-benzylglycine benzyl ester

N²-(6,7-dimethoxy-2-naphthalenesulfonyl)-N-benzyl-N-(3-carboxypropyl)-L-argininamide N²-(6,7-dimethoxy-2-naphthalenesulfonyl)-N-benzyl-N-(3-tert-butoxycarbonylpropyl)-L-argininamide N²-(4,6-dimethoxy-2-naphthalenesulfonyl)-L-arginyl-N-phenethyl-β-alanine N²-(4,6-dimethoxy-2-naphthalenesulfonyl)-L-arginyl-N-phenethyl-β-alanine tert-butyl ester N²-(6,7-dimethoxy-2-naphthalenesulfonyl)-L-arginyl-N-benzylglycine phenyl ester N²-(6-methoxy-2-naphthalenesulfonyl)-L-arginyl-N-(3-phenylpropyl)glycine N²-(6-methoxy-2-naphthalenesulfonyl)-L-arginyl-N-(3-phenylpropyl)glycine tert-butyl ester N²-(5-methoxy-1-naphthalenesulfonyl)-L-arginyl-N-benzyl-β-alanine N²-(5-methoxy-1-naphthalenesulfonyl)-L-arginyl-N-benzyl-β-alanine tert-butyl ester

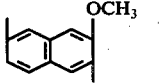

| Sample No. | $R_1$ | $R_2$ | $R_3$ | n | Addition moiety | Concentration required to prolong the coagulation time by a factor of two (μM) | Preparation process (Ex. No.) | m.p. (° C) | Elementary analysis Upper: Calculated Lower: Found | | | I.R. (KBr) (cm$^{-1}$) |
|---|---|---|---|---|---|---|---|---|---|---|---|---|
| | | | | | | | | | C | H | N | |
| 1 |  | 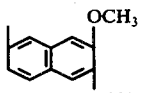 | C(CH₃)₃ | 1 | 0.5 H₂SO₃ | | 2 | 189–191 (dec) | 55.68 55.36 | 6.33 6.35 | 10.47 10.45 | 3,360 cm$^{-1}$ 3,160 cm$^{-1}$ 1,730 cm$^{-1}$ |
| 2 |  | 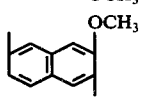 | H | 1 | — | | 2 | powder | 56.73 56.43 | 5.82 5.80 | 12.25 12.19 | 3,370 cm$^{-1}$ 3,200 cm$^{-1}$ 1,615 cm$^{-1}$ |
| 3 |  | 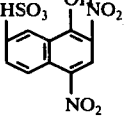 | C(CH₃)₃ | 2 | 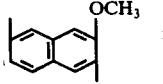 | | 2 | 132–135 (dec) | 52.78 52.61 | 5.17 5.15 | 10.26 10.23 | 3,360 cm$^{-1}$ 3,80 cm$^{-1}$ 1,720 cm$^{-1}$ |
| 4 |  | 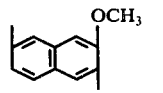 | H | 2 | — | | 2 | powder | 57.42 57.19 | 6.02 6.10 | 11.96 11.73 | 3,360 cm$^{-1}$ 3,160 cm$^{-1}$ 1,620 cm$^{-1}$ |
| 5 | 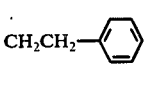 | 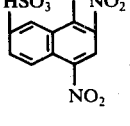 | C(CH₃)₃ | 1 | (see structure) | | 2 | 157–158 (dec) | 52.78 52.63 | 5.17 5.14 | 10.26 10.09 | 3,380 cm$^{-1}$ 3,220 cm$^{-1}$ 1,750 cm$^{-1}$ |

-continued

Structure:
$$\text{HN} = \underset{H_2N}{\overset{}{C}} - \overset{H}{N} - CH_2CH_2CH_2\overset{R_2}{\underset{H-N-SO_2}{\overset{|}{C}H}}CON\underset{(CH_2)_n-COOR_3}{\overset{R_2}{|}}$$
$$\overset{|}{R_1}$$

| Sample No. | $R_1$ | $R_2$ | $R_3$ | n | Addition moiety | Concentration required to prolong the coagulation time by a factor of two (μM) | Preparation process (Ex. No.) | m.p. (°C) | Elementary analysis Upper: Calculated Lower: Found C | H | N | I.R. (KBr) (cm⁻¹) |
|---|---|---|---|---|---|---|---|---|---|---|---|---|
| 6 | naphthyl-2,3-di-OCH₃ | CH₂CH₂-phenyl | H | 1 | — | 3.0 | 1 | powder | 57.42 / 57.09 | 6.02 / 6.06 | 11.96 / 11.74 | 3,360 cm⁻¹ / 3,200 cm⁻¹ / 1,590 cm⁻¹ |
| 7 | naphthyl-2,3-di-OCH₃ | CH₂CH₂-phenyl | C(CH₃)₃ | 2 | HSO₃-naphthyl-OH,NO₂,NO₂ | | 2 | 155–157 (dec) | 53.25 / 53.13 | 5.30 / 5.21 | 10.11 / 10.03 | 3,380 cm⁻¹ / 3,180 cm⁻¹ / 1,720 cm⁻¹ |
| 8 | naphthyl-2,3-di-OCH₃ | CH₂CH₂-phenyl | H | 2 | — | | 1 | powder | 50.08 / 57.93 | 6.22 / 6.04 | 11.68 / 11.54 | 3,200– / 3,380 cm⁻¹ (broad) / 1,620 cm⁻¹ |
| 9 | naphthyl-1,4-di-OCH₃ | CH₂-phenyl | C(CH₃)₃ | 1 | HSO₃-naphthyl-OH,NO₂,NO₂ | | 2 | 153–156 (dec) | 52.58 / 52.14 | 5.03 / 4.98 | 10.41 / 10.36 | 3,400 cm / 3,080 cm / 1,740 cm |
| 10 | naphthyl-1,4-di-OCH₃ | CH₂-phenyl | H | 1 | — | | 2 | powder | 56.73 / 56.58 | 5.82 / 5.73 | 12.25 / 12.14 | 3,000– / 3,400 cm⁻¹ (broad) / 1,600 cm⁻¹ |
| 11 | naphthyl-2-OCH₃ | CH₂-phenyl | C(CH₃)₃ | 3 | HSO₃-naphthyl-OH,NO₂,NO₂ | | 2 | 144–148 (dec) | 53.67 / 53.69 | 5.26 / 5.24 | 10.43 / 10.39 | 3,360 cm⁻¹ / 3,200 cm⁻¹ / 1,720 cm⁻¹ |
| 12 | naphthyl-2-OCH₃ | CH₂-phenyl | H | 3 | — | | 2 | powder | 59.04 / 59.14 | 6.19 / 16.15 | 12.30 / 12.28 | 3,040– / 3,360 cm⁻¹ (broad) / 1,610 cm⁻¹ |
| 13 | naphthyl-2-OCH₃ | CH₂-phenyl | C(CH₃)₃ | 2 | HSO₃-naphthyl-OH,NO₂,NO₂ | | 2 | 155–158 (dec) | 53.19 / 54.97 | 5.12 / 5.06 | 10.59 / 10.48 | 3,400 cm⁻¹ / 3,200 cm⁻¹ / 1,730 cm⁻¹ |
| 14 | naphthyl-7-OCH₃ | CH₂-phenyl | H | 2 | — | | 1 | powder | 58.37 / 58.19 | 6.00 / 5.98 | 12.61 / 12.49 | 3,300 cm⁻¹ (broad) / 1,640 cm⁻¹ |
| 15 | naphthyl-7-OCH₃ | CH₂CH₂-phenyl | C(CH₃)₃ | 1 | HSO₃-naphthyl-OH,NO₂,NO₂ | | 2 | 147–150 (dec) | 59.19 / 59.23 | 5.12 / 5.07 | 10.59 / 10.54 | 3,400 cm⁻¹ / 3,230 cm⁻¹ / 1,750 cm⁻¹ |
| 16 | naphthyl-7-OCH₃ | CH₂CH₂-phenyl | H | 1 | — | | 1 | powder | 58.37 / 58.21 | 6.00 / 5.93 | 12.61 / 12.46 | 3,200 cm⁻¹ (broad) / 1,620 cm⁻¹ |
| 17 | naphthyl-5-CH₃-8-OCH₃ | CH₂-phenyl | C(CH₃)₃ | 1 | — | | 2 | powder | 60.29 / 60.21 | 6.58 / 6.56 | 11.72 / 11.64 | 3,365 cm⁻¹ / 3,170 cm⁻¹ / 1,730 cm⁻¹ |

-continued

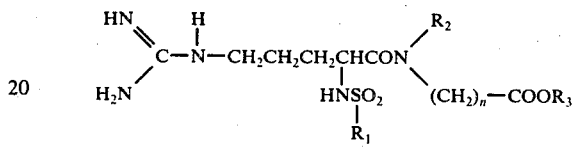

| Sample No. | $R_1$ | $R_2$ | $R_3$ | n | Addition moiety | Concentration required to prolong the coagulation time by a factor of two (μM) | Preparation process (Ex. No.) | m.p. (° C) | Elementary analysis Upper: Calculated Lower: Found | | | I.R. (KBr) (cm$^{-1}$) |
| --- | --- | --- | --- | --- | --- | --- | --- | --- | --- | --- | --- | --- |
| | | | | | | | | | C | H | N | |
| 18 | [5-methyl-8-methoxy-naphthyl] | $CH_2$—phenyl | H | 1 | — | 2.0 | 2 | powder | 57.66 57.48 | 5.77 5.74 | 12.93 12.84 | 3,360 cm$^{-1}$ 3,160 cm$^{-1}$ 1,610 cm$^{-1}$ |

Many amino acid tert-butyl esters, for use as starting materials in the invention, have not been previously reported in the chemical literature but can be synthesized by the aforementioned procedure of Example 2 (C) which is essentially that as taught by A. J. Speziale et al., J. Org. Chem., 25 731 (1960). For example, the following esters have been so synthesized:

| No. | Amino Acid tert-Butyl Ester | B.P. |
| --- | --- | --- |
| 1 | HN(CH$_2$CH$_2$—phenyl)(CH$_2$CO$_2$-t-C$_4$H$_9$) | 166° C/10 mm Hg |
| 2 | HN(CH$_2$—phenyl)(CH$_2$CH$_2$CO$_2$-t-C$_4$H$_9$) | 164° C/14 mm Hg |
| 3 | HN(CH$_2$—phenyl)(CH$_2$CH$_2$CH$_2$CO$_2$-t-C$_4$H$_9$) | 123° C/2 mm Hg |

Having now fully described the invention, it will be apparent to one of ordinary skill in the art that many changes and modifications can be made thereto without departing from the spirit or scope of the invention as set forth herein.

What is claimed as new and intended to be secured by Letters Patent of the United States is:

1. $N^2$-alkoxynaphthalenesulfonyl-L-argininamides having the formula:

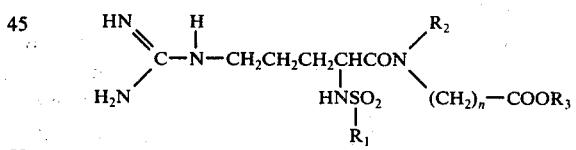

and the pharmaceutically acceptable salts thereof, wherein $R_1$ is naphthyl substituted with at least one $C_1$–$C_5$ alkoxy; $R_2$ is $C_7$–$C_{15}$ aralkyl; $R_3$ is $C_1$–$C_{10}$ alkyl, $C_6$–$C_{10}$ aryl or $C_7$–$C_{12}$ aralkyl; and n is an integer of 1, 2 or 3.

2. The compound of claim 1, wherein $R_1$ is naphthyl substituted with one or two $C_1$–$C_3$ alkoxy; $R_2$ is $C_7$–$C_{10}$ aralkyl; and $R_3$ is $C_1$–$C_6$ alkyl, phenyl or $C_7$–$C_{10}$ aralkyl.

3. The compound of claim 1, wherein $R_1$ is selected from the group consisting of 5-methoxy-1-naphthyl, 6-methoxy-2-naphthyl, 7-methoxy-2-naphthyl, 4,6-dimethoxy-2-naphthyl, 6,7-dimethoxy-2-naphthyl and 6,7-diethoxy-2-naphthyl; $R_2$ is selected from the group consisting of benzyl, phenethyl and 3-phenyl-propyl; and $R_3$ is methyl, ethyl, tertbutyl, phenyl or benzyl.

4. A method for inhibiting activity and suppressing activation of thrombin in vivo, which comprises administering to a mammal a pharmaceutically effective amount of an $N^2$-alkoxynaphthalenesulfonyl-L-argininamide having the formula:

or the pharmaceutically acceptable salts thereof, wherein $R_1$ is naphthyl substituted with at least one $C_1$–$C_5$ alkoxy; $R_2$ is $C_7$–$C_{15}$ aralkyl; $R_3$ is $C_1$–$C_{10}$ alkyl, $C_6$–$C_{10}$ aryl or $C_7$–$C_{12}$ aralkyl; and n is an integer of 1, 2 or 3.

* * * * *

UNITED STATES PATENT AND TRADEMARK OFFICE
CERTIFICATE OF CORRECTION

PATENT NO. : 4,069,318
DATED : January 17, 1978
INVENTOR(S) : Okamoto et al

It is certified that error appears in the above-identified patent and that said Letters Patent are hereby corrected as shown below:

Please correct the Foreign Application information to read as follows:

--[30] Foreign Application Priority Data

| Nov. 8, 1974 | Japan | 49-128774 |
| Nov. 8, 1974 | Japan | 49-128775 |
| Nov. 29, 1974 | Japan | 49-136695 |
| Nov. 29, 1974 | Japan | 49-136697 |
| Feb. 25, 1975 | Japan | 50-023268 |
| Feb. 26, 1975 | Japan | 50-023635 |
| March 5, 1975 | Japan | 50-026768 |
| March 11, 1975 | Japan | 50-029357 |
| March 11, 1975 | Japan | 50-029358-- |

Signed and Sealed this

Twenty-seventh Day of June 1978

[SEAL]

Attest:

RUTH C. MASON
Attesting Officer

DONALD W. BANNER
Commissioner of Patents and Trademarks